(12) United States Patent
Lee et al.

(10) Patent No.: US 7,892,780 B2
(45) Date of Patent: Feb. 22, 2011

(54) METHOD FOR SCREENING ANTIOXIDANT USING MUTANT BACTERIA AND CHLOROPHYLLIDE, AND ANTIOXIDANT SCREENED BY THE METHOD

(75) Inventors: Jeong-Kug Lee, Seoul (KR); Hae-Jin Rhee, Namyangju-Si (KR); Eui-Jin Kim, Seoul (KR); Moon-Hee Sung, Daejeon (KR)

(73) Assignees: Industry-University Cooperation Foundation Sogang University, Seoul (KR); Kookmin University Industry Academy Cooperation Foundation Kookmin University, Seoul (KR)

( * ) Notice: Subject to any disclaimer, the term of this patent is extended or adjusted under 35 U.S.C. 154(b) by 224 days.

(21) Appl. No.: 12/011,275

(22) Filed: Jan. 24, 2008

(65) Prior Publication Data
US 2008/0305511 A1 Dec. 11, 2008

(30) Foreign Application Priority Data

Feb. 24, 2007 (KR) .................. 10-2007-0018752
Nov. 6, 2007 (KR) .................. 10-2007-0112892

(51) Int. Cl.
*C12Q 1/26* (2006.01)
(52) U.S. Cl. .................. 435/25; 435/325; 435/7.1; 435/6; 435/252
(58) Field of Classification Search .................. None
See application file for complete search history.

(56) References Cited

FOREIGN PATENT DOCUMENTS

KR 10-2007-0059485 6/2007

OTHER PUBLICATIONS

Scott et al. (The Journal of Biological Chemistry, vol. 262, No. 8, Issue of Mar. 15, pp. 3640-3645, 1987.*
McCord, J., et al., "Superoxide Dismutase, An Enzymic Function for Erythrocuprein (Hemocuprein)", The Journal of Biological Chemistry, vol. 244, No. 22, Nov. 25, 1969, pp. 6049-6055.
Imlay, James A., "Pathways of Oxidative Damage", Annu. Rev. Microbiol. 2003, 57, pp. 395-418.

* cited by examiner

*Primary Examiner*—Hope A Robinson
(74) *Attorney, Agent, or Firm*—Christie, Parker & Hale, LLP (57) ABSTRACT

Disclosed is a method for screening an antioxidant using mutant bacteria and chlorophyllide, and an antioxidant screened by the same method. The method provides for screening of an antioxidant by monitoring growth profiles of specific mutant bacteria in filter discs or medium blocks containing chlorophyllide added thereto, and an antioxidant screened by the same method. By monitoring growth profiles of mutant bacteria using mutant bacteria and chlorophyllide, screening of an antioxidant is possible on an industrial scale. In particular, the antioxidant screening method is useful for selective screening of an amphiphilic antioxidant. Therefore, it is possible to screen and commercialize low-toxic and effective antioxidants used in various food and cosmetic additives, as well as therapeutic medicines.

8 Claims, 3 Drawing Sheets
(3 of 3 Drawing Sheet(s) Filed in Color)

SEQUENCE LISTING

<160> NUMBER OF SEQ ID NOS: 13

<210> SEQ ID NO 1
<211> LENGTH: 1002
<212> TYPE: DNA
<213> ORGANISM: Rhodobacter sphaeroides

<400> SEQUENCE: 1

```
atgacggatg cacccgaact gaaggcgttc gaccaacgcc tccgcgacga ggcggcggaa        60
gagccgacgc tcgaggtgcc gcaaggcgag ccgaagaaga agacgcaggt catcgcgatc       120
tacggcaagg gcggcatcgg caagagcttc acgctggcga acctcagcta catgatggcc       180
cagatcggca agcgcgtgct gctgatcggc tgcgacccga agtccgacac gacctcgctt       240
ctgttcggcg gcaaggcctg ccccacgatc atcgagacct cggccaggaa gaagctggcc       300
ggcgaagagg tccagatcgg cgacgtctgc ttcaagcgcg acggcgtctt cgcgatggag       360
ctgggcgggc ccgaggtggg ccgcggctgc ggcgggcgcg gcatcatcca cggcttcgaa       420
ctgctggaga agctcggctt ccacgactgg gacttcgact atgtgctgct cgacttcctg       480
ggcgacgtgg tctgcggcgg cttcggcctg cccatcgccc gcgacatggc gcagaaggtg       540
atcctcgtcg gatcgaacga cctccagtcg ctctatgtga cgaacaacgt ctgctcggcg       600
gtggaatatt tccgcaagct cggcggcaac gtgggcgtgg cggggctcgt catcaacaag       660
gacgacggca ccggcgaggc caaggccttc gccgaggcgg cggacattcc gatccttgcg       720
acgattccgg ccgacgagga tctgcgccgc aagtcggcga actatcagat cgtcggcatt       780
cccggcacgc aatggggacc tctcttcgag gggctggccc atgccgtggg cgaggcgccc       840
ccgatccggc cgaagccgct gtcgcaggat ggcctcctcg acctcttcac ccccgaggcg       900
atcggcgccg acttcaagct cgagcccgcc acggatgccg acatgcgcgg caagaacgcg       960
gccgcgaaga atcgctgga agtgatctac gacgatgctt ga                         1002
```

<210> SEQ ID NO 2
<211> LENGTH: 1509
<212> TYPE: DNA
<213> ORGANISM: Rhodobacter sphaeroides

<400> SEQUENCE: 2

-continued

| | |
|---|---|
| atgagccaga ccccaggcgg cgccccgatg gcgcccgagg ccatgggctg ccattccacg | 60 |
| gccgacatgg ccgccgcggc cagtgccgcg ggcaacggcg aactgatgga gcggttcaag | 120 |
| gccgactatc cggtcgggcc ccacgacaag ccgcagagca tgtgcccggc cttcgggtcg | 180 |
| ctgcgcaccg ggcttcggat gcggcggtg gcacgatca tctcgggttc ggcctgctgc | 240 |
| acctacggcc tctcgttcgt ctcgcatttc tacggcgcgc ggcggtcgat cggctatgtg | 300 |
| cccttcaatt cggaatcgct cgtcacgggc aagctgttcg aggacatccg cgaggcggtc | 360 |
| cacgagatgg ccgatccgca cgcctatgac gcgatcgtgg tgacgaacct ctgcgtgccg | 420 |
| accgcctcgg gcgtgccgct gcggctcctg ccctccgaga tcaacggcgt gcggatcgtg | 480 |
| ggcatcgacg tgccgggctt cggcgtgccg acccatgccg aggcgaagga cgtgctggcg | 540 |
| ggcgcgatgc tgaaatatgc cgctccgag atcgaggcgg gcccggtgca ggcgccggtc | 600 |
| tcgggccggt ccgaccggcc gaccgtggcg ctgctgggcg agatgttccc ggccgatccg | 660 |
| gtgatgatcg gggcgctgct ggcgccgctg ggtcttgctg cggggcccgt ggtgccctgc | 720 |
| cgcgactggc gcgagctcta tgccgcgctc gacagtggcg tggccgcggc gatccatccc | 780 |
| ttctacacgg cctcggtccg cgagtttcag gccgcaggcc gcgccatcgt gggctctgcc | 840 |
| cccgtgggcc atgacggcac cgccgcctgg cttgccgcca tcggcgaggc ctatggcatc | 900 |
| gccgccgaca aggtggccgc gcgcagaac gccttcctgc ccgcgatcag gggcgcgctg | 960 |
| gccggtgcgc cgatcaaggg gcgcatcacg ctctcgggct atgagggctc cgagctgatc | 1020 |
| gtggcgcgcc tgctgatcga gagcggcgcc gaagtgccct atgtgggcac cgccgcaggc | 1080 |
| aggacgccct ggagtgccgc cgaccgcgaa tggctcgagg cccggggcac ggtggtgaag | 1140 |
| ttccgcgcct cgctcgagga cgatctcgcc gcgatgcagg gcttcgagcc cgacctcgcc | 1200 |
| gtgggcacga ccccggtggt gcagaaggcc aagtcgctgg gcatcccgtc gctctacttc | 1260 |
| accaacctca tctcggcccg gccgctgatg gggccggccg gagcgggcag cctcgcgcag | 1320 |
| gtgatcaatg cggccatcgg caaccgcgag cggatgtcga agatgaaagc cttcttcgcc | 1380 |
| ggcgtaggcg aggggggatac ggccggcatc tgggagggtg cgcccaacct gcgccccgac | 1440 |
| ttccgggccg cgcaccagaa gaagctcgag aaggccgccc gggccgccaa gtccgaggag | 1500 |
| atgatctga | 1509 |

<210> SEQ ID NO 3
<211> LENGTH: 1476
<212> TYPE: DNA
<213> ORGANISM: Rhodobacter sphaeroides

<400> SEQUENCE: 3

| | |
|---|---|
| atgctcgtgc aggatcatga cagggcaggg ggctactggg gcgccgtcta tgccttctgt | 60 |
| gcggtgaagg ggcttcaggt ggtgatcgac ggccccgtgg gctgcgagaa cctgccggtg | 120 |
| acctcggtgc tgcattacac cgacgcgctg cccccgcacg agctgcccat cgtggtgacg | 180 |
| ggcctcggcg agagcgagat gagcgagggc accgaggcct cgatgagccg ggcctggaag | 240 |
| gtgctggatc cggcgctgcc cgcggtggtg gtcacgggct cgatcgccga gatgatcggc | 300 |
| ggcggcgtga cgccgcaggg cacgaacatc cagcgcttcc tgccccgcac catcgacgag | 360 |
| gaccagtggg aagcggccga ccgggcgatg acctggatct tctcggagtt cgggatgacc | 420 |
| aagggtcgca tgccgcccga agccaagcgc cccgaggggg cgaagccgcg ggtgaacatc | 480 |
| ctcgggccca tgtacggcgt cttcaacatg gcgtcggacc ttcacgagat tcgccgtctc | 540 |

-continued

```
gtcgagggga tcggcgccga agtgaacatg gtgatgccct tgggcgcgca tctggccgag      600
atgcgacact tggtcaatgc cgacgccaac atcgtcatgt accgcgaatt cggccgcggg      660
ctggccgagg tgctgggcaa gccctacctc caggccccca tcggggtcga gagcacgacc      720
gccttcctgc gccgcctggg cgagattctg gcctcgatcc ggagcccctt catcgagcgc      780
gagaagcact cgacgctgaa gcccgtgtgg gatctgtggc ggagtgtcac gcaggacttc      840
ttcgggacgg ccaatttcgg aatcgtggcg accgaaactt atgcaagagg catccgaaac      900
tatctcgaag gcgatctcgg gctgccctgc gccttcgccg tggcccgcaa gaggggctcg      960
aagaccgaca acgaagcggt gcgcggactg atccgccagc accgtccgct cgtgctcatg     1020
gggtcgatca acgagaagat ttaccttgcg gaactgaaag ccggtcacgg cccgcaaccc     1080
tctttcatcg ctgcctcttt cccgggtgcg gcgatccggc gcgctaccgg aacgcccgtt     1140
atgggatatg caggtgctac gtggttactg caggaagttt gcaacgccct gttcgacgcc     1200
ctgttccaca tttctgcccct cgggacggag atggacagcg ccgccgccac accgacgaca     1260
ctgcgccgcg acttcccgtg ggatgccgat gcgcaagcgg ccctggaccg catcgtagag     1320
gagcatccgg ttctcacccg gatcagcgcc gcgcgtgcct tgcgcgacgc cgccgagaag     1380
gctgccctcg atgccggtgc cgagagggtc gtgagagaga ctgtcgaagc cctgcgtggg     1440
ccgggcttcg gcgagaggaa gggagagaac caatga                               1476
```

<210> SEQ ID NO 4
<211> LENGTH: 18
<212> TYPE: DNA
<213> ORGANISM: Artificial Sequence
<220> FEATURE:
<223> OTHER INFORMATION: forward primer of bchX

<400> SEQUENCE: 4
caccggatcc cggatgca                                                     18

<210> SEQ ID NO 5
<211> LENGTH: 21
<212> TYPE: DNA
<213> ORGANISM: Artificial Sequence
<220> FEATURE:
<223> OTHER INFORMATION: forward primer of bchY

<400> SEQUENCE: 5
ggcaggagga tccgccagac c                                                 21

<210> SEQ ID NO 6
<211> LENGTH: 18
<212> TYPE: DNA
<213> ORGANISM: Artificial Sequence
<220> FEATURE:
<223> OTHER INFORMATION: forward primer of bchZ

<400> SEQUENCE: 6
gatctagatc tcgtgcag                                                     18

<210> SEQ ID NO 7
<211> LENGTH: 18
<212> TYPE: DNA
<213> ORGANISM: Artificial Sequence
<220> FEATURE:
<223> OTHER INFORMATION: reverse primer of bchX

<400> SEQUENCE: 7
cgcgcgaagc tttcgaga                                                     18

<210> SEQ ID NO 8
<211> LENGTH: 18
<212> TYPE: DNA
<213> ORGANISM: Artificial Sequence
<220> FEATURE:
<223> OTHER INFORMATION: reverse primer of bchY

<400> SEQUENCE: 8
tgtcataagc ttgcacga                                              18

<210> SEQ ID NO 9
<211> LENGTH: 18
<212> TYPE: DNA
<213> ORGANISM: Artificial Sequence
<220> FEATURE:
<223> OTHER INFORMATION: reverse primer of bchZ

<400> SEQUENCE: 9
cggaagcttc gctcattg                                              18

<210> SEQ ID NO 10
<211> LENGTH: 302
<212> TYPE: DNA
<213> ORGANISM: Artificial Sequence
<220> FEATURE:
<223> OTHER INFORMATION: rrnB promoter

<400> SEQUENCE: 10
cgtcgcgcgc accctctgcg gcggccggac gactcaccgg aggctctgag tcgccgcgca      60
ggtcgggcga aagggcgggt cgccggctc cgcggcaacg aaaaacgcca agatttcttg     120
gctgcgacat gaaattgtta cggagcccaa aaaatccgct tgcgcccggg gccgtctgct    180
cctagaaacc gcttcaccga gacgaagacc ggcagcgccg gacggagacg agggagcgga    240
tgacagaaac gtcggccgcg acaattgaag atgaggcgga cgggatcgct ggttgtctgg    300
cg                                                                   302

<210> SEQ ID NO 11
<211> LENGTH: 333
<212> TYPE: PRT
<213> ORGANISM: Rhodobacter sphaeroides

<400> SEQUENCE: 11

Met Thr Asp Ala Pro Glu Leu Lys Ala Phe Asp Gln Arg Leu Arg Asp
  1               5                  10                  15

Glu Ala Glu Glu Pro Thr Leu Glu Val Pro Gln Gly Glu Pro Lys
             20                  25                  30

Lys Lys Thr Gln Val Ile Ala Ile Tyr Gly Lys Gly Ile Gly Lys
         35                  40                  45

Ser Phe Thr Leu Ala Asn Leu Ser Tyr Met Met Ala Gln Ile Gly Lys
 50                  55                  60

Arg Val Leu Leu Ile Gly Cys Asp Pro Lys Ser Asp Thr Thr Ser Leu
 65                  70                  75                  80

Leu Phe Gly Gly Lys Ala Cys Pro Thr Ile Ile Glu Thr Ser Ala Arg
                 85                  90                  95

Lys Lys Leu Ala Gly Glu Glu Val Gln Ile Gly Asp Val Cys Phe Lys
            100                 105                 110

Arg Asp Gly Val Phe Ala Met Glu Leu Gly Gly Pro Glu Val Gly Arg
        115                 120                 125

-continued

```
Gly Cys Gly Gly Arg Gly Ile Ile His Gly Phe Glu Leu Leu Glu Lys
        130                 135                 140

Leu Gly Phe His Asp Trp Asp Phe Asp Tyr Val Leu Leu Asp Phe Leu
145                 150                 155                 160

Gly Asp Val Val Cys Gly Gly Phe Gly Leu Pro Ile Ala Arg Asp Met
                165                 170                 175

Ala Gln Lys Val Ile Leu Val Gly Ser Asn Asp Leu Gln Ser Leu Tyr
            180                 185                 190

Val Thr Asn Asn Val Cys Ser Ala Val Glu Tyr Phe Arg Lys Leu Gly
        195                 200                 205

Gly Asn Val Gly Val Ala Gly Leu Val Ile Asn Lys Asp Asp Gly Thr
    210                 215                 220

Gly Glu Ala Lys Ala Phe Ala Glu Ala Ala Asp Ile Pro Ile Leu Ala
225                 230                 235                 240

Thr Ile Pro Ala Asp Glu Asp Leu Arg Arg Lys Ser Ala Asn Tyr Gln
                245                 250                 255

Ile Val Gly Ile Pro Gly Thr Gln Trp Gly Pro Leu Phe Glu Gly Leu
            260                 265                 270

Ala His Ala Val Gly Glu Ala Pro Pro Ile Arg Pro Lys Pro Leu Ser
        275                 280                 285

Gln Asp Gly Leu Leu Asp Leu Phe Thr Pro Glu Ala Ile Gly Ala Asp
    290                 295                 300

Phe Lys Leu Glu Pro Ala Thr Asp Ala Asp Met Arg Gly Lys Asn Ala
305                 310                 315                 320

Ala Ala Lys Lys Ser Leu Glu Val Ile Tyr Asp Ala
                325                 330

<210> SEQ ID NO 12
<211> LENGTH: 502
<212> TYPE: PRT
<213> ORGANISM: Rhodobacter sphaeroides

<400> SEQUENCE: 12

Met Ser Gln Thr Pro Gly Gly Ala Pro Met Ala Pro Glu Ala Met Gly
1               5                   10                  15

Cys His Ser Thr Ala Asp Met Ala Ala Ala Ser Ala Ala Gly Asn
                20                  25                  30

Gly Glu Leu Met Glu Arg Phe Lys Ala Asp Tyr Pro Val Gly Pro His
            35                  40                  45

Asp Lys Pro Gln Ser Met Cys Pro Ala Phe Gly Ser Leu Arg Thr Gly
        50                  55                  60

Leu Arg Met Arg Arg Val Gly Thr Ile Ile Ser Gly Ser Ala Cys Cys
65                  70                  75                  80

Thr Tyr Gly Leu Ser Phe Val Ser His Phe Tyr Gly Ala Arg Arg Ser
                85                  90                  95

Ile Gly Tyr Val Pro Phe Asn Ser Glu Ser Leu Val Thr Gly Lys Leu
            100                 105                 110

Phe Glu Asp Ile Arg Glu Ala Val His Glu Met Ala Asp Pro Gln Arg
        115                 120                 125

Tyr Asp Ala Ile Val Val Thr Asn Leu Cys Val Pro Thr Ala Ser Gly
    130                 135                 140

Val Pro Leu Arg Leu Leu Pro Ser Glu Ile Asn Gly Val Arg Ile Val
145                 150                 155                 160

Gly Ile Asp Val Pro Gly Phe Gly Val Pro Thr His Ala Glu Ala Lys
                165                 170                 175
```

```
Asp Val Leu Ala Gly Ala Met Leu Lys Tyr Ala Arg Ser Glu Ile Glu
            180                 185                 190

Ala Gly Pro Val Gln Ala Pro Val Ser Gly Arg Ser Asp Arg Pro Thr
        195                 200                 205

Val Ala Leu Leu Gly Glu Met Phe Pro Ala Asp Pro Val Met Ile Gly
    210                 215                 220

Ala Leu Leu Ala Pro Leu Gly Leu Ala Ala Gly Pro Val Val Pro Cys
225                 230                 235                 240

Arg Asp Trp Arg Glu Leu Tyr Ala Ala Leu Asp Ser Gly Val Ala Ala
                245                 250                 255

Ala Ile His Pro Phe Tyr Thr Ala Ser Val Arg Glu Phe Gln Ala Ala
            260                 265                 270

Gly Arg Ala Ile Val Gly Ser Ala Pro Val Gly His Asp Gly Thr Ala
        275                 280                 285

Ala Trp Leu Ala Ala Ile Gly Glu Ala Tyr Gly Ile Ala Ala Asp Lys
    290                 295                 300

Val Ala Ala Ala Gln Asn Ala Phe Leu Pro Ala Ile Arg Gly Ala Leu
305                 310                 315                 320

Ala Gly Ala Pro Ile Lys Gly Arg Ile Thr Leu Ser Gly Tyr Glu Gly
                325                 330                 335

Ser Glu Leu Ile Val Ala Arg Leu Leu Ile Glu Ser Gly Ala Glu Val
            340                 345                 350

Pro Tyr Val Gly Thr Ala Ala Gly Arg Thr Pro Trp Ser Ala Ala Asp
        355                 360                 365

Arg Glu Trp Leu Glu Ala Arg Gly Thr Val Val Lys Phe Arg Ala Ser
    370                 375                 380

Leu Glu Asp Asp Leu Ala Ala Met Gln Gly Phe Glu Pro Asp Leu Ala
385                 390                 395                 400

Val Gly Thr Thr Pro Val Val Gln Lys Ala Lys Ser Leu Gly Ile Pro
                405                 410                 415

Ser Leu Tyr Phe Thr Asn Leu Ile Ser Ala Arg Pro Leu Met Gly Pro
            420                 425                 430

Ala Gly Ala Gly Ser Leu Ala Gln Val Ile Asn Ala Ala Ile Gly Asn
        435                 440                 445

Arg Glu Arg Met Ser Lys Met Lys Ala Phe Phe Ala Gly Val Gly Glu
    450                 455                 460

Gly Asp Thr Ala Gly Ile Trp Glu Gly Ala Pro Asn Leu Arg Pro Asp
465                 470                 475                 480

Phe Arg Ala Ala His Gln Lys Lys Leu Glu Lys Ala Ala Arg Ala Ala
                485                 490                 495

Lys Ser Glu Glu Met Ile
            500

<210> SEQ ID NO 13
<211> LENGTH: 491
<212> TYPE: PRT
<213> ORGANISM: Rhodobacter sphaeroides

<400> SEQUENCE: 13

Met Leu Val Gln Asp His Asp Arg Ala Gly Gly Tyr Trp Gly Ala Val
1               5                   10                  15

Tyr Ala Phe Cys Ala Val Lys Gly Leu Gln Val Val Ile Asp Gly Pro
            20                  25                  30

Val Gly Cys Glu Asn Leu Pro Val Thr Ser Val Leu His Tyr Thr Asp
```

```
                35                  40                  45
Ala Leu Pro Pro His Glu Leu Pro Ile Val Val Thr Gly Leu Gly Glu
             50                  55                  60
Ser Glu Met Ser Glu Gly Thr Glu Ala Ser Met Ser Arg Ala Trp Lys
 65                  70                  75                  80
Val Leu Asp Pro Ala Leu Pro Ala Val Val Val Thr Gly Ser Ile Ala
                 85                  90                  95
Glu Met Ile Gly Gly Val Thr Pro Gln Gly Thr Asn Ile Gln Arg
                100                 105                 110
Phe Leu Pro Arg Thr Ile Asp Glu Asp Gln Trp Glu Ala Ala Asp Arg
                115                 120                 125
Ala Met Thr Trp Ile Phe Ser Glu Phe Gly Met Thr Lys Gly Arg Met
            130                 135                 140
Pro Pro Glu Ala Lys Arg Pro Glu Gly Ala Lys Pro Arg Val Asn Ile
145                 150                 155                 160
Leu Gly Pro Met Tyr Gly Val Phe Asn Met Ala Ser Asp Leu His Glu
                165                 170                 175
Ile Arg Arg Leu Val Glu Gly Ile Gly Ala Glu Val Asn Met Val Met
            180                 185                 190
Pro Leu Gly Ala His Leu Ala Glu Met Arg His Leu Val Asn Ala Asp
            195                 200                 205
Ala Asn Ile Val Met Tyr Arg Glu Phe Gly Arg Gly Leu Ala Glu Val
210                 215                 220
Leu Gly Lys Pro Tyr Leu Gln Ala Pro Ile Gly Val Glu Ser Thr Thr
225                 230                 235                 240
Ala Phe Leu Arg Arg Leu Gly Glu Ile Leu Gly Leu Asp Pro Glu Pro
                245                 250                 255
Phe Ile Glu Arg Glu Lys His Ser Thr Leu Lys Pro Val Trp Asp Leu
                260                 265                 270
Trp Arg Ser Val Thr Gln Asp Phe Phe Gly Thr Ala Asn Phe Gly Ile
            275                 280                 285
Val Ala Thr Glu Thr Tyr Ala Arg Gly Ile Arg Asn Tyr Leu Glu Gly
            290                 295                 300
Asp Leu Gly Leu Pro Cys Ala Phe Ala Val Ala Arg Lys Arg Gly Ser
305                 310                 315                 320
Lys Thr Asp Asn Glu Ala Val Arg Gly Leu Ile Arg Gln His Arg Pro
                325                 330                 335
Leu Val Leu Met Gly Ser Ile Asn Glu Lys Ile Tyr Leu Ala Glu Leu
            340                 345                 350
Lys Ala Gly His Gly Pro Gln Pro Ser Phe Ile Ala Ala Ser Phe Pro
            355                 360                 365
Gly Ala Ala Ile Arg Arg Ala Thr Gly Thr Pro Val Met Gly Tyr Ala
370                 375                 380
Gly Ala Thr Trp Leu Leu Gln Glu Val Cys Asn Ala Leu Phe Asp Ala
385                 390                 395                 400
Leu Phe His Ile Leu Pro Leu Gly Thr Glu Met Asp Ser Ala Ala Ala
                405                 410                 415
Thr Pro Thr Thr Leu Arg Arg Asp Phe Pro Trp Asp Ala Asp Ala Gln
                420                 425                 430
Ala Ala Leu Asp Arg Ile Val Glu Glu His Pro Val Leu Thr Arg Ile
            435                 440                 445
Ser Ala Ala Arg Ala Leu Arg Asp Ala Ala Glu Lys Ala Ala Leu Asp
450                 455                 460
```

```
Ala Gly Ala Glu Arg Val Val Arg Glu Thr Val Glu Ala Leu Arg Gly
465                 470                 475                 480

Pro Gly Phe Gly Glu Arg Lys Gly Glu Asn Gln
                485                 490
```

METHOD FOR SCREENING ANTIOXIDANT USING MUTANT BACTERIA AND CHLOROPHYLLIDE, AND ANTIOXIDANT SCREENED BY THE METHOD

CROSS-REFERENCE TO RELATED APPLICATION

This application claims priority to and the benefit of Korean Patent Application Nos. 10-2007-0018752 and 10-2007-0112892, filed in the Korean Intellectual Property Office on Feb. 24, 2007, and Nov. 6, 2007, respectively, the entire content of which is incorporated herein by reference.

BACKGROUND OF THE INVENTION

1. Field of the Invention

The present invention relates to a method for screening an antioxidant using mutant bacteria and chlorophyllide. More specifically, the present invention relates to a method for easy screening of an antioxidant by monitoring growth profiles of certain mutant bacteria in filter discs or medium blocks with addition of chlorophyllide, and an antioxidant screened by the same method.

2. Description of the Related Art

As is generally known to those skilled in the art, reactive oxygen species (ROS) or oxygen-free radicals have undesirable oxidizing properties in the body, by which such molecular species contribute to damage of cell membranes, DNA and diverse cell structures and is responsible, either directly or indirectly, for pathogenic causes of various diseases such as cancer, arteriosclerosis, diabetes, cerebral apoplexy, myocardial infarction, hepatitis, nephritis, atopic diseases, Parkinson's disease, and the like. Superoxide is a reactive oxygen species and is produced by reduction of molecular oxygen to the superoxide anion ($O^{2-}$) via acceptance of an additional one electron in the course of the oxygen metabolism process in living organisms. Superoxide is highly reactive to thereby result in irreversible destruction of biomaterials constituting the organisms, such as nucleic acids, proteins, and lipids. In particular, superoxide reduces $Fe^{3+}$ ions into $Fe^{2+}$ ions when $Fe^{3+}$ ions are present, and the thus-reduced $Fe^{2+}$ ions react with hydrogen peroxide to form hydroxy radicals. The hydroxy radicals thus formed react with DNA molecules in vivo, which consequently is known to bring about inhibition of metabolism and homeostasis of the organisms, such as in vivo mutagenesis, destruction of iron-sulfur (Fe/S) centers of proteins, peroxidation of lipids, and the like (Imlay, J. A., 2003, Ann. Rev. Microbiol. 57: 395-418).

Therefore, a great deal of importance is given to antioxidant materials which are capable of reducing the cytotoxicity of reactive oxygen species including superoxide anion radicals or are capable of directly inactivating the reactive oxygen species, and various methods have been developed for screening desired antioxidants. For example, antioxidants have been assayed and developed by a method using changes in colors or fluorescence of putative candidate materials through the in vitro redox reaction, a method of using DNA chain cleavage or a method of using spin trap agents which are capable of specifically reacting with reactive oxygen species. However, most of the antioxidants which were developed by these methods suffer from limited uses and applications thereof due to low bioavailability arising from substantial in vivo absorption or the potential risk of toxicity to the organisms. Further, because the aforementioned methods involve in vitro examination of an antioxidant activity, in vivo efficiency, safety and antioxidant specificity of the antioxidant candidate must be verified by repeated multiple screening processes.

In spite of excellent biomembrane permeability and bioavailability as well as a high antioxidant activity, fat-soluble antioxidants may cause deleterious effects on cell body since they are mostly localized in diverse intracellular membranes, which makes it difficult to exert the antioxidant action at aqueous target site where reactive oxygen species are produced. Also, it is difficult for the fat-soluble antioxidants to be metabolized into more hydrophilic forms in liver after reacting with ROS or RNS (reactive nitrogen species), which facilitate excretion of the hydrophobic chemicals from the body. On the other hand, the water-soluble antioxidants exhibit smooth external excretion of the oxidized antioxidants, but have low biomembrane permeability which raises various problems associated with cell membrane-protective effects and difficulty of diffusion of the antioxidant into intracellular organelles. Therefore, there is a need for development of an amphiphilic antioxidant which can be easily formulated into a desired antioxidant preparation, by having both water-solubility and fat-solubility in order to comply with desired uses and applications of the antioxidant.

Meanwhile, microorganisms of the genus *Rhodobacter* which are purple non-sulfur photosynthetic bacteria exhibit advantages such as no evolution of oxygen during the photosynthetic process unlike algal or plant photosynthesis, and capability to grow and proliferate under various culture conditions, e.g. aerobic conditions, anaerobic dark conditions and anaerobic light conditions. In particular, the members of the phototrophic *Rhodobacter* genus carry out a series of cell membrane-associated electron transfer processes by absorption of long-wavelength light via the photosynthetic apparatus containing bacteriochlorophyll pigments under the anaerobic light conditions, which results in conversion of light energy into chemical energy, and the thus-generated chemical energy is used as energy necessary for a variety of cell metabolic activities such as carbon dioxide fixation. In the photosynthetic bacteria, a multimeric protein, which is one of the enzymes that mediate the metabolic process for synthesis of bacteriochlorophyll and is produced by expression of three genes bchX, bchY and bchZ, is known to have chlorophyllide-reducing activities.

Korean Patent Application Publication No. 2007-59485 A1 discloses a multimeric protein as a superoxide-generating enzyme derived from *Rhodobacter sphaeroides*. According to this patent, the multimeric protein produces superoxide in vivo and in vitro when chlorophyllide as an amphiphilic substrate exists, so it is possible to selectively kill cells that express the multimeric protein. However, this patent publication merely mentions a function of the multimeric protein as a superoxide-generating reagent, but does not suggest details and schemes for practical application of such a protein to an antioxidant screening method.

SUMMARY OF THE INVENTION

Therefore, the present invention has been made in view of the above problems, and it is an object of the present invention to provide a method for screening an antioxidant, which is capable of selectively screening an amphiphilic antioxidant on an industrial scale through a simple method.

It is another object of the present invention to provide an antioxidant screened by the aforesaid method.

In accordance with an aspect of the present invention, the above and other objects can be accomplished by the provision of a method for screening an antioxidant using mutant bacteria and chlorophyllide, comprising:

culturing mutant bacteria on an agar plate medium, wherein the bacteria have an inhibited superoxide dismutase activity by incorporation of a mutation into a superoxide dismutase-encoding gene sequence;

placing a plurality of filter discs with addition of antioxidant candidate materials to be screened and chlorophyllide on the agar plate medium; and selecting the filter discs where growth of mutant bacteria is observed.

In accordance with another aspect of the present invention, there is provided a method for screening an antioxidant using mutant bacteria and chlorophyllide, comprising:

adding chlorophyllide to an agar plate medium for bacterial culture and cutting the agar plate medium into a block form to thereby prepare a plurality of chlorophyllide-added medium blocks;

placing a plurality of the medium blocks on a Petri dish for bacterial culture;

adding to a plurality of the medium blocks, antioxidant candidate materials to be screened and mutant bacteria having an inhibited superoxide dismutase activity by incorporation of a mutation into a superoxide dismutase-encoding gene sequence; and selecting the medium blocks where growth of the mutant bacteria is observed.

In one preferred embodiment of the present invention, the mutant bacteria may express chlorophyllide reductase which is a multimeric protein inducing production of superoxide anions in the presence of oxygen.

In another preferred embodiment of the present invention, the mutant bacteria may be *Rhodobacter sphaeroides, Rhodospirillum rubrum, Rhodopseudomonas palustris, Allochromatium vinosum, Chlorobium tepidum* or *Chloroflexus aurantiacus*.

In another preferred embodiment of the present invention, the mutant bacteria may be transformed to over-express chlorophyllide reductase which is a multimeric protein inducing production of superoxide anions in the presence of oxygen.

In another preferred embodiment of the present invention, the transformation of the bacteria into which mutation is to be introduced (hereinafter, referred to as "mutation target bacteria") may be carried out by:

preparing a first recombinant vector having an inhibited superoxide dismutase activity by incorporation of a mutation into a superoxide dismutase-encoding gene sequence and a second recombinant expression vector capable of over-expressing a multimeric protein that induces production of superoxide anions in the presence of oxygen;

preparing first transformant *E. coli* with introduction of the first recombinant vector and second transformant *E. coli* with introduction of the second recombinant expression vector, using the first recombinant vector and the second recombinant expression vector, respectively; and conjugating the first and second transformant *E. coli* with the mutation target bacteria to construct mutant bacteria.

In another preferred embodiment of the present invention, the transformed bacteria may be *Rhodobacter sphaeroides* 2.4.1 SodB1 [KCTC 11069BP].

In another preferred embodiment of the present invention, the mutant bacteria do not produce hydrogen peroxide in the presence of chlorophyllide under an oxygen concentration of 1 to 3%, and can have an activity of producing superoxide anions.

In another preferred embodiment of the present invention, an amount of chlorophyllide added to the filter disc or the agar plate medium may be in a range of 0.1 mM to 100 mM.

In another preferred embodiment of the present invention, the filter disc may have a diameter of 5 mm to 20 mm and a thickness of 0.1 mm to 1 mm, and the medium block may have a diameter of 10 mm to 30 mm and a thickness of 5 mm to 15 mm.

In accordance with yet another aspect of the present invention, there is provided an antioxidant screened by the aforesaid method.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Hereinafter, the present invention will be described in more detail.

The present invention is directed to a method for selective screening of a desired antioxidant from various candidate materials, using chlorophyllide and mutant bacteria, and an antioxidant screened by the same method. The antioxidant screening method provides easy screening of the desired antioxidant by monitoring growth profiles of certain mutant bacteria in filter discs or medium blocks to which chlorophyllide was added.

The present invention provides construction of the mutant photosynthetic bacteria having an inhibited superoxide dismutase activity by incorporation of a mutation into a superoxide dismutase-encoding gene sequence.

Wild-type bacteria may exhibit alleviation of superoxide-mediated cytotoxicity owing to the expression of superoxide dismutase that converts the generated superoxide anions into hydrogen peroxide, whereas the mutant bacteria in accordance with the present invention, due to suppression of a superoxide dismutase activity, exhibit relatively significant superoxide-mediated cytotoxicity, as compared to the wild-type bacteria.

Therefore, the mutant bacteria in accordance with the present invention will be killed due to the presence of superoxide anions produced by the enzymatic action of the multimeric protein on chlorophyllide, but will inhibit the cytotoxicity of superoxide anions when a certain candidate material having an antioxidant activity is present among candidate materials to be screened. As a result, the mutant bacteria can survive and grow, which thereby enables easy screening of candidate materials having an antioxidant activity based on whether the mutant bacteria grow or not.

Figure 1:
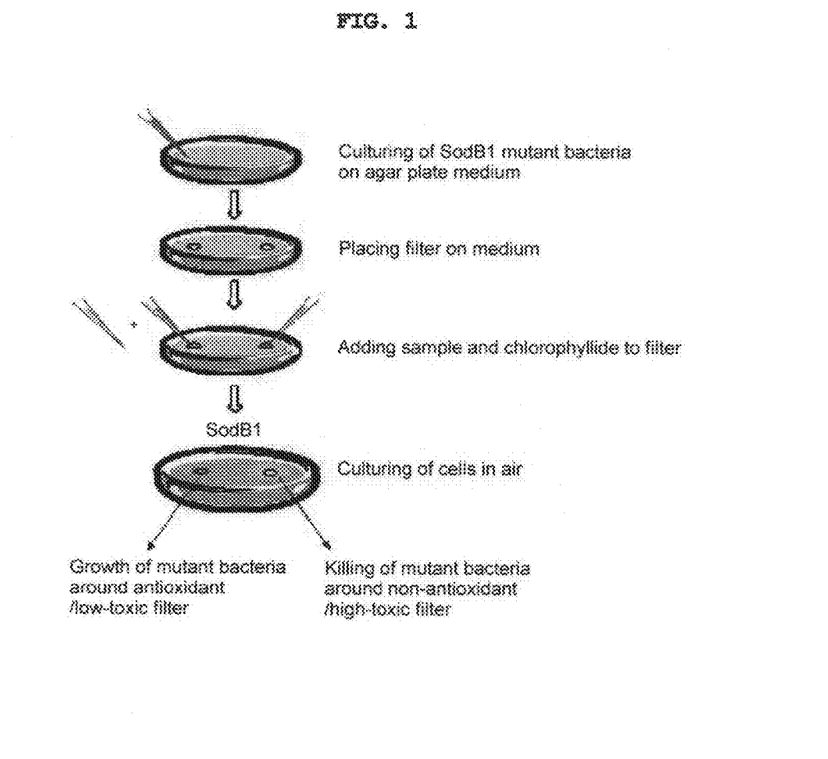
FIG. 1 is a schematic process chart showing an antioxidant screening method using a plurality of filter discs with addition of chlorophyllide, as an example of a method for screening an antioxidant in accordance with the present invention.

Specifically, the antioxidant screening method in accordance with the present invention includes culturing mutant bacteria on an agar plate medium, wherein the bacteria have an inhibited superoxide dismutase activity by incorporation of a mutation into a superoxide dismutase-encoding gene sequence; placing a plurality of filter discs with addition of antioxidant candidate materials to be screened and chlorophyllide on the agar plate medium; and selecting the filter discs where growth of mutant bacteria is observed. FIG. 1 shows a schematic process chart for the antioxidant screening method.

The aforesaid method employs a plurality of filter discs for addition of chlorophyllide and antioxidant candidate materials, after cell culture of the mutant bacteria.

Figure 2:
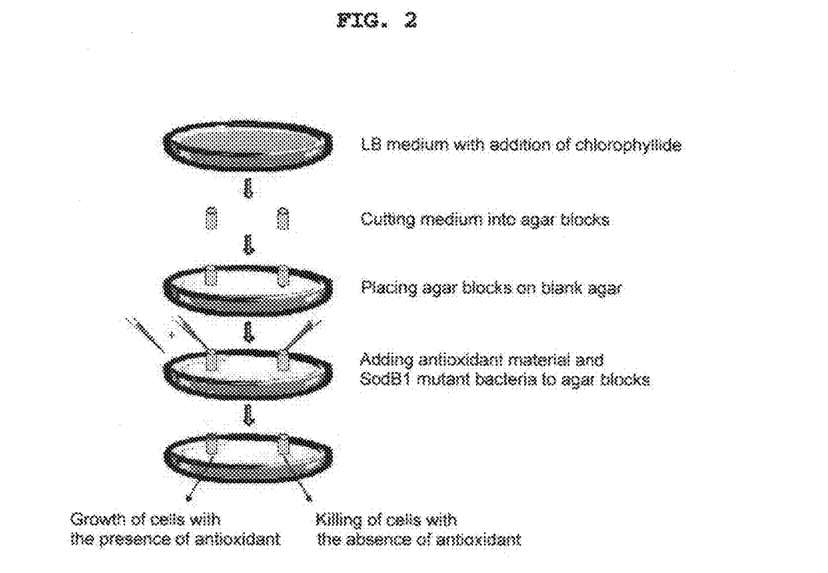
FIG. 2 is a schematic process chart showing an antioxidant screening method using a plurality of medium blocks, as another example of an antioxidant screening method in accordance with the present invention.

Alternatively, the antioxidant screening method may also be carried out by preparation of medium blocks with addition of chlorophyllide, followed by addition of the mutant bacteria and the antioxidant candidate materials. This antioxidant screening method in accordance with the present invention includes adding chlorophyllide to an agar plate medium for bacterial cultivation and cutting the agar plate medium into a block form to thereby prepare a plurality of chlorophyllide-added medium blocks; placing a plurality of the medium blocks on a Petri dish for bacterial culture; adding to a plurality of the medium blocks, antioxidant candidate materials to be screened and mutant bacteria having an inhibited superoxide dismutase activity by incorporation of a mutation into a superoxide dismutase-encoding gene sequence; and selecting the medium blocks where growth of mutant bacteria is observed. FIG. 2 shows a schematic process chart for such an antioxidant screening method.

In particular, the antioxidant screening method in accordance with the present invention is useful for easy screening of an amphiphilic antioxidant having both water-solubility and fat-solubility. That is, when the antioxidant candidate material has no water-solubility characteristics, solubility of the material in the filter disc or medium block is lowered to result in poor intracellular diffusion of the antioxidant material. On the other hand, when the antioxidant candidate material has no fat-solubility characteristics, this may result in deterioration of cell membrane permeability to thereby lower intracellular absorptivity, so it is impossible to effectively inhibit superoxide-mediated toxicity. Therefore, according to the antioxidant screening method of the present invention, antioxidant candidate materials which are amphiphilic antioxidants help effective growth of the mutant bacteria.

The mutant bacteria of the present invention may be capable of expressing chlorophyllide reductase which is a multimeric protein inducing production of superoxide anions in the presence of oxygen. Specific examples of the mutant bacteria include, but are not limited to, photosynthetic bacteria such as *Rhodobacter sphaeroides, Rhodospirillum rubrum, Rhodopseudomonas palustris, Allochromatium vinosum, Chlorobium tepidum* and *Chloroflexus aurantiacus*.

Even if the mutant bacteria of the present invention were incapable of expressing the chlorophyllide reductase, they may be transformed to express chlorophyllide reductase. Such bacteria are disclosed in Korean Patent Application Publication No. 2007-59485 A1, by transformation of the bacteria with a recombinant expression vector containing bchX (SEQ ID NO: 1), bchY (SEQ ID NO: 2) and bchZ (SEQ ID NO: 3) genes, an rrnB promoter and an N-terminal His-tag. The thus-expressed multimeric protein functions as a reductase that utilizes chlorophyllide as a substrate, which thereby produces superoxide anions.

Transformation of the mutant bacteria may be carried out by preparing a first recombinant vector having an inhibited superoxide dismutase activity by incorporation of a mutation into a superoxide dismutase-encoding gene sequence and a second recombinant expression vector capable of expressing a multimeric protein that induces production of superoxide anions in the presence of oxygen; preparing first transformant *E. coli* with introduction of the first recombinant vector and second transformant *E. coli* with introduction of the second recombinant expression vector, using the first recombinant vector and the second recombinant expression vector, respectively; and conjugating the first and second transformant *E. coli* with the mutation target bacteria to construct mutant bacteria.

For example, the present inventors selected *Rhodobacter sphaeroides* as the mutation target bacteria, and prepared a recombinant vector for disruption of a superoxide dismutase gene. Then, *E. coli* was transformed with the thus-prepared recombinant vector to thereby prepare the transformant *E. coli*. Finally, mutant bacteria were constructed by conjugation of the transformant *E. coli* with *Rhodobacter sphaeroides*. The thus-constructed mutant bacteria are SodB1 variants that has an inhibited superoxide dismutase activity while being capable of expressing the multimeric protein reducing chlorophyllide, which were designated *Rhodobacter sphaeroides* 2.4.1 SodB1 and deposited under Accession Number KCTC 11069BP on Feb. 12, 2007.

The mutant bacteria constructed according to the present invention express the multimeric protein, and the thus-expressed multimeric protein can have an activity of producing superoxide anions while not producing hydrogen peroxide under an oxygen concentration of 1 to 3% because the multimeric protein reduces chlorophyllide. Conventional superoxide-generating materials, such as methyl viologen, plumbagin, menadione and the like, produce hydrogen peroxide as well as superoxide, as the resulting products. However, the resulting hydrogen peroxide ($H_2O_2$) presents various problems. For example, the reaction of $H_2O_2$ with iron ions ($Fe^{2+}$) leads to production of hydroxy radicals which consequently brings about fatty degeneration or DNA variation. Further, due to high cell membrane permeability and relative stability, the aforementioned superoxide-generating materials may exhibit adverse side effects on normal cells other than target cells where hydrogen peroxide was produced. For these reasons, it was necessary to remove hydrogen peroxide via separate treatment of catalase. However, the multimeric protein, which is expressed by the mutant bacteria constructed according to the present invention, has a capability to produce superoxide anions without evolution of hydrogen peroxide, so it is possible to overcome limitations and problems suffered by conventional arts.

In the antioxidant screening method of the present invention, an amount of chlorophyllide added to the filter disc or the agar plate medium may be in a range of 0.1 mM to 100 mM. If a content of chlorophyllide is lower than 0.1 mM, the sensitivity is too low. On the other hand, if a content of chlorophyllide is higher than 100 mM, this may undesirably cause cytotoxicity.

A size of the filter disc or chlorophyllide-added medium block placed on the agar plate medium or Petri dish may vary depending upon numbers of the screening-target candidate material or taking into consideration easiness and convenience of visual observation. For example, the filter disc may have a diameter of 5 to 20 mm and a thickness of 0.1 to 1 mm, and the medium block may have a diameter of 10 to 30 mm and a thickness of 5 to 15 mm.

Further, the present invention provides an antioxidant screened by the aforesaid screening method.

For example, as will be demonstrated in the following examples, Pch212 among antioxidants screened by the screening method of the present invention has amphiphilic properties, and therefore exhibits excellent solubility in both DMSO (dimethylsulfoxide) and water-soluble buffers. Further, as can be seen from the observation results of bacterial growth of FIG. 4, Pch212 has a superior antioxidant activity, as compared to a conventional antioxidant, fat-soluble quercetin or fat-soluble tocopherol.

In conclusion, the present invention enables easy and selective screening of an amphiphilic antioxidant on an industrial scale, by monitoring growth profiles of mutant bacteria via use of mutant bacteria and chlorophyllide.

EXAMPLES

Now, the present invention will be described in more detail with reference to the following Examples. These examples are provided only for illustrating the present invention and should not be construed as limiting the scope and spirit of the present invention.

Example 1

Construction of Mutant Bacteria 1.1 Construction of Multimeric Protein-Expressing Mutant Bacteria Polymerase chain reaction (PCR) was carried out for fusion of a His-tag or Strep-tag to N-termini of bchX (SEQ ID NO: 1), bchY (SEQ ID NO: 2) and bchZ (SEQ ID NO: 3) genes. Forward primers were modified at a translation initiation codon (ATG). For this purpose, primers of SEQ ID NO: 4, SEQ ID NO: 5 and SEQ ID NO: 6 were prepared and used for bchX, bchY and bchZ genes, respectively. Backward primers were prepared to have HindIII recognition sites. For this purpose, primers of SEQ ID NO: 7, SEQ ID NO: 8 and SEQ ID NO: 9 were prepared and used for bchX, bchY and bchZ genes, respectively. Underlines shown in Table 1 below represent base sequences which were optionally modified to prepare restriction enzyme recognition sites, and base sequences represented by thick black lines are recognition sequences of corresponding restriction enzymes.

TABLE 1

| SEQ ID NO: | Primers | Sequences (5'→3') | Remarks |
|---|---|---|---|
| 4 | Forward primer | CACCGGATCCCGGATGCA | BamHI recognition sequence |
| 5 | Forward primer | GGCAGGA GGAT CCGCCAGACC | BamHI recognition sequence |
| 6 | Forward primer | GATCTAGATCTCGTGCAG | BgIII recognition sequence |

TABLE 1-continued

| SEQ ID NO: | Primers | Sequences (5'→3') | Remarks |
|---|---|---|---|
| 7 | Backward primer | CGCGCGAAGCTTTCGAGA | HindIII recognition sequence |
| 8 | Backward primer | TGTCATAAGCTTGCACGA | HindIII recognition sequence |
| 9 | Backward primer | CGGAAGCTTCGCTCATTG | HindIII recognition sequence |

For bchX and bchY genes, PCR products obtained with these primers were restricted with BamHI and HindIII and ligated into a pRSET-C vector (Invitrogen) whose BamHI and HindIII recognition sites were cleaved, thereby constructing pRSET-HisX and pRSET-HisY vectors, respectively. Cleavage to obtain DNA fragments was carried out using the corresponding restriction enzyme (restriction endonuclease, TAKARA, Japan), and ligation of DNA fragments was carried out using T4 DNA ligase (TAKARA, Japan). Further, the PCR amplification product of the bchZ gene was digested with BglII and HindIII and cloned into BamHI and HindIII sites of a pRSET-C vector, thereby constructing a pRSET-HisZ vector. Using the XbaI site which is located 142 bp upstream from the BamHI site of the pRSET-C vector, each XbaI-HindIII fragment was obtained from pRSET-HisX, pRSET-HisY and pRSET-HisZ vectors. The thus-obtained restriction fragment was cloned into a vector containing an rrnB promoter of *Rhodobacter sphaeroides* in a pRK415 vector, thereby constructing pRK-HisX, pRK-HisY and pRK-HisZ vectors, respectively. These vectors are designed to express the genes encoding a desired protein containing a His-tag fused to the N-terminus thereof under the control of the rrnB promoter (SEQ ID NO: 10) and express a desired protein containing a His-tag fused to the N-terminus thereof. Each of these vector constructs was transformed into the strain *E. coli* S17-1, and then mobilized into *Rhodobacter sphaeroides* by a conjugation process. In order to obtain desired transformants, transformed *E. coli* cells were plated on a Sistrom's minimal medium with supplementation of tetracycline as an antibiotic marker which is capable of selecting for the vector plasmid, and antibiotic-resistant bacterial strains were then picked out. Expression of BchX, BchY and BchZ proteins was confirmed by Western blot analysis using antibodies against His-tags.

In order to confirm the expression of desired proteins, BchX (SEQ ID NO: 11), BchY (SEQ ID NO: 12) and BchZ (SEQ ID NO: 13) proteins were over-expressed in these transformant bacterial strains, followed by separation of the proteins. Individual bacterial strains containing pRK-HisX, pRK-HisY and pRK-HisZ vector constructs were cultured anaerobically in a 1 L culture media bottle which was capped with a cap made of a butyl synthetic rubber and was purged with nitrogen gas. The separation of proteins was carried out in an anaerobic chamber (Model 10, COY, Grass Lake, Mich.) containing 5% hydrogen, 5% carbon dioxide, and 90% nitrogen. In order to obtain water-soluble, overexpressed proteins present in cultured cells, cell disruption was carried out using a sonicator (Sonifier 250, Branson, Sweden) at a temperature of 4° C. for 10 min, and the resulting cell lysates were centrifuged at 4° C. and 12,000 g to thereby obtain a water-soluble cytosolic fraction which was then subjected to protein separation using nickel-affinity chromatography (Qiagen)

according to the manufacturer instructions. For this purpose, the cytosolic fraction was attached to a nickel resin. Through the competitive affinity of individual proteins for imidazole, BchX, BchY and BchZ proteins were obtained. For elution of the proteins, 50 mM sodium dihydrogen phosphate ($NaH_2PO_4$) buffer (pH 7.9) containing 150 mM imidazole and 300 mM sodium chloride was used. Confirmation of individual proteins was carried out by 12% polyacrylamide gel electrophoresis. As a result, expression of proteins BchX, BchY and BchZ was confirmed as protein bands of 40 kDa, 58 KDa, and 57 kDa, respectively (FIG. 3).

Figure 3:
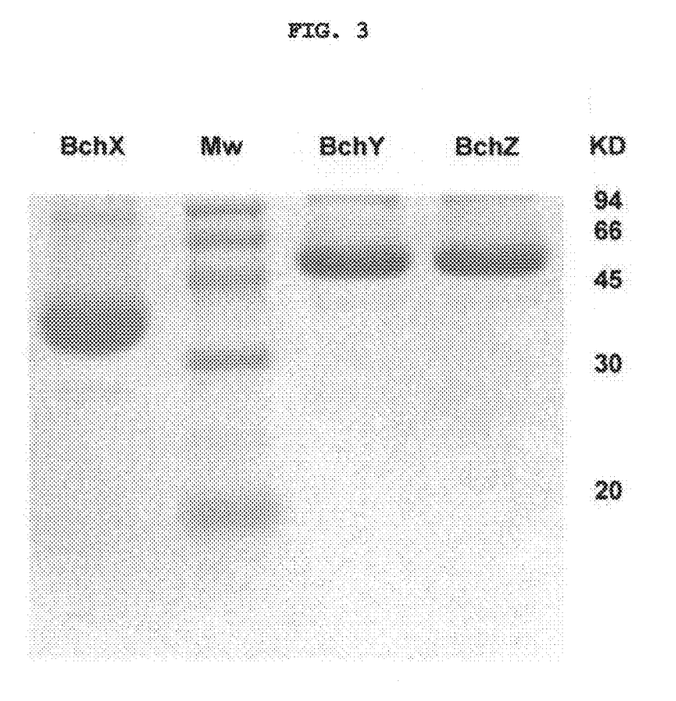
FIG. 3 is a photograph showing the results of SDS-PAGE using 12% polyacrylamide gel, following purification of a target protein after expression of BchX, BchY and BchZ genes into a recombinant protein with a His-tag in *E. coli*.

FIG. 3 is a photograph showing protein electrophoresis (SDS-PAGE) patterns on a 12% polyacrylamide gel, after separation of BchX, BchY and BchZ proteins from *Rhodobacter sphaeroides* culture fractions. Each of Lanes represents separated proteins (BchX, BchY, and BchZ). In order to confirm sizes of individual proteins, proteins having standard molecular weight were also electrophoresed.

These bchX, bchY and bchZ genes were positioned on one vector, and the resulting plasmid vector was mobilized by a conjugation process, which consequently results in expression of all the proteins BchX, BchY and BchZ. As a result, desired transformed mutant bacteria were constructed which are capable of constitutively expressing chlorophyllide reductase.

1.2 Construction of SodB1 Variant

Using the mutant bacteria prepared in Section 1.1 of Example 1, SodB1 variant bacteria, which have an inhibited superoxide dismutase activity due to incorporation of a mutation into a superoxide dismutase-encoding gene sequence, were constructed according to the following method.

An iron-superoxide dismutase (Fe-SOD)-encoding sodB gene was disrupted through the induction of homologous recombination using a pLO1 suicide vector. A transcription/translation terminator containing a streptomycin/spectinomycin resistance gene was inserted into a StuI site of the sodB gene, and the resulting gene structure was cloned into a suicide vector to thereby construct a pLO1-B1 vector. Upon homologous recombination using the resulting pLO1-B1 vector construct, colonies with double-crossover homologous recombination were selected which exhibit antibiotic resistance only against streptomycin and spectinomycin due to the presence of the streptomycin/spectinomycin resistance gene in the middle of the gene and show no vector-mediated kanamycin resistance, and sodB1-defective mutant strains were then picked out.

The SodB1 variant expressing the multimeric protein, i.e. *Rhodobacter sphaeroides* 2.4.1 SodB1, was deposited with KTCC under Accession Number KCTC 11069BP on Feb. 12, 2007.

Example 2

Isolation of Chlorophyllide

In order to isolate chlorophyllide which is a substrate for the multimeric protein expressed from mutant bacteria of Example 1, the bchZ gene of *Rhodobacter sphaeroides* was disrupted through the induction of homologous recombination. In order to construct bchZ-defective mutant, restriction endonuclease BamHI was used which recognizes and cleaves the BamHI restriction site present in the bchZ gene. For this purpose, *Rhodobacter sphaeroides* was digested with BalI and PstI to obtain a bchZ gene region, and then a transcription/translation terminator containing a kanamycin resistance gene was inserted into the BamHI region of the bchZ gene. The resulting gene construct was cloned into a suicide vector pSUP202 to construct a pSUP-BZ vector. Upon homologous recombination using the resulting pSUP-BZ vector, colonies with the double-crossover homologous recombination event were selected which exhibit antibiotic resistance only against kanamycin due to the presence of the kanamycin resistance gene in the middle of the gene and show no vector-mediated tetracycline resistance, and bchZ-defective mutant strains were then picked out. When they were allowed to grow under anaerobic dark conditions using dimethylsulfoxide as a final electron acceptor of the electron transfer chain, the bchZ-defective mutant strains exhibited accumulation of green chlorophyllide in the culture medium. Upon measurement of chlorophyllide using a spectrophotometer (UV-2550, Shimadzu, Japan), the results of absorbance at a wavelength of 663 nm were obtained as previously reported in conventional arts. In order to separate chlorophyllide accumulated in the culture medium, the medium was extracted with diethyl ether, dried over nitrogen and dissolved in dimethylsulfoxide for use in subsequent reaction.

Example 3

Screening of Antioxidants

As shown in FIGS. 1 and 2, an agar plate medium supplemented with chlorophyllide (0.1 to 100 mM) was prepared, cut into very tiny medium blocks, and then placed on a blank agar plate. Next, an antioxidant sample and SodB1 mutant bacteria were added to these medium blocks, or otherwise chlorophyllide (0.1 to 100 mM) was added directly to filter discs to which a desired concentration of an antioxidant candidate material was then added. Thereafter, multimeric protein-expressing SodB1 mutant bacteria, i.e. *Rhodobacter sphaeroides* 2.4.1 SodB1 [KCTC 11069BP], were plated on a Sistrom's minimal medium [20 mM potassium dihydrogen phosphate ($KH_2PO_4$), 3.8 mM ammonium sulfate (($NH_4$)$_2$$SO_4$), 34 mM succinic acid, 0.59 mM L-glutamic acid, 0.30 mM L-aspartic acid, 8.5 mM sodium chloride, 1.05 mM nitrilotriacetic acid, 1.2 mM magnesium chloride ($MgCl_2.6H_2O$), 0.23 mM calcium chloride ($CaCl_2.7H_2O$), 25 µM ferrous sulfate ($FeSO_4.7H_2O$), 0.16 µM ammonium molybdate (($NH_4$)$6Mo_7O_{24}.4H_2O$), 4.7 µM EDTA, 38 µM zinc sulfate ($ZnSO_4.7H_2O$), 9.1 µM manganese sulfate ($MnSO_4.H_2O$), 1.6 µM copper sulfate ($CuSO_4.5H_2O$), 0.85 µM cobalt (II) nitrate ($Co(NO_3)_2.6H_2O$), 1.8 µM boric acid ($H_3BO_3$), 8.1 µM nicotinic acid, 1.5 µM thiamine hydrochloride, and 41 nM biotin] (Sistrom, W. R, 1962. J. Gen. Microbiol. 28: 607-616).

Figure 4:
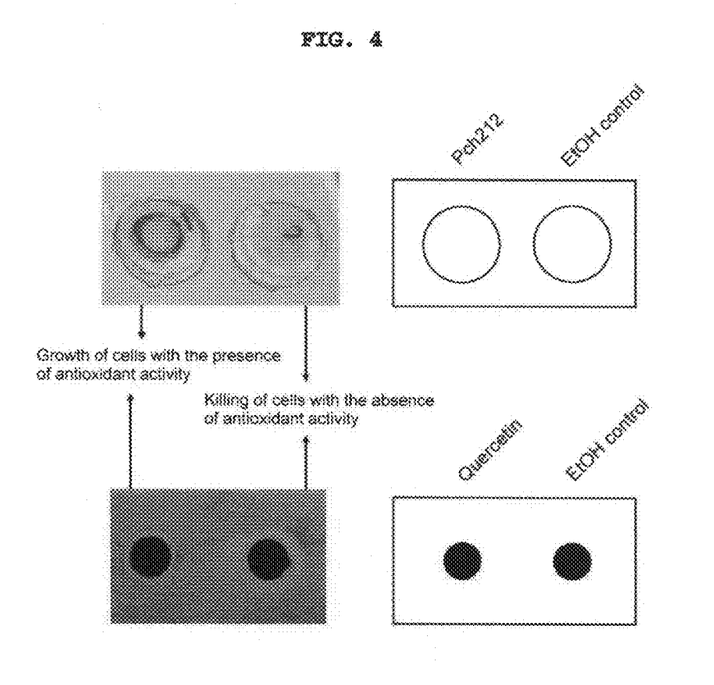
FIG. 4 is a photograph showing the comparison results of bacterial growth profiles observed in the presence or absence of an antioxidant activity in an antioxidant candidate material, upon screening of an antioxidant using medium blocks in accordance with the present invention.

As a result, when there was an antioxidant activity in the antioxidant candidate material to be screened, cells grew only on the medium blocks or around filter discs and thus red bacteria were observed. When there was no antioxidant activity in the antioxidant candidate material, all of the cells were killed with no observation of red cell growth. Further, when the screening-target antioxidant candidate material has the antioxidant activity, the cells also grew around the filter discs and therefore red bacteria were observed. On the other hand, the antioxidant candidate material contains no antioxidant activity, the cells around the filter discs were killed (FIG. 4).

The cell cultures of numerous bacteria were extracted with ethanol, methanol, diethyl ether, acetone and chloroform, respectively, and the resulting extracts were dried over nitrogen. Antioxidant activities of the thus-obtained extracts were examined as described above, and one potent antioxidant was designated Pch212. In order to compare the antioxidant activity of Pch212 with that of a conventional antioxidant, Pch212 was dissolved at a suitable concentration in an ethanol or dimethylsulfoxide solvent to thereby examine the antioxidant activity of the target material. The results thus obtained are shown in FIG. 5.

Figure 5:
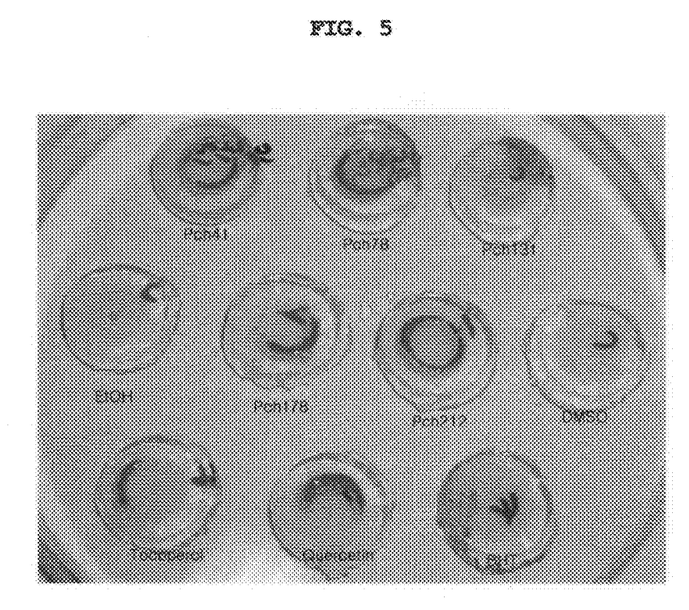
FIG. 5 is a photograph showing the observation results of bacterial growth profiles for comparison of an antioxidant activity of an antioxidant Pch212 screened according to the present invention with that of a conventional antioxidant.

As shown in FIG. 5, a negative control group, e.g. ethanol or dimethylsulfoxide, exhibited no cell growth, whereas fat-soluble quercetin or fat-soluble tocopherol having a potent antioxidant activity showed partial cell growth. Pch212 exhibited the most effective prevention of cell death. Further, when Pch212 was dissolved in DMSO and water-soluble buffer in order to confirm amphiphilic properties of Pch212, Pch212 exhibited excellent solubility in both solvents.

Example 4

Antioxidant Effects of Pch212 on Superoxide Anions

The antioxidant activity of the antioxidant Pch212 screened by the amphiphilic antioxidant screening method was confirmed by cytochrome reduction. The cytochrome reduction was carried out with a modification of a conventional method (McCord and Fridovich, 1969, J. Biol. Chem. 244: 6049-6055).

Figure 6:
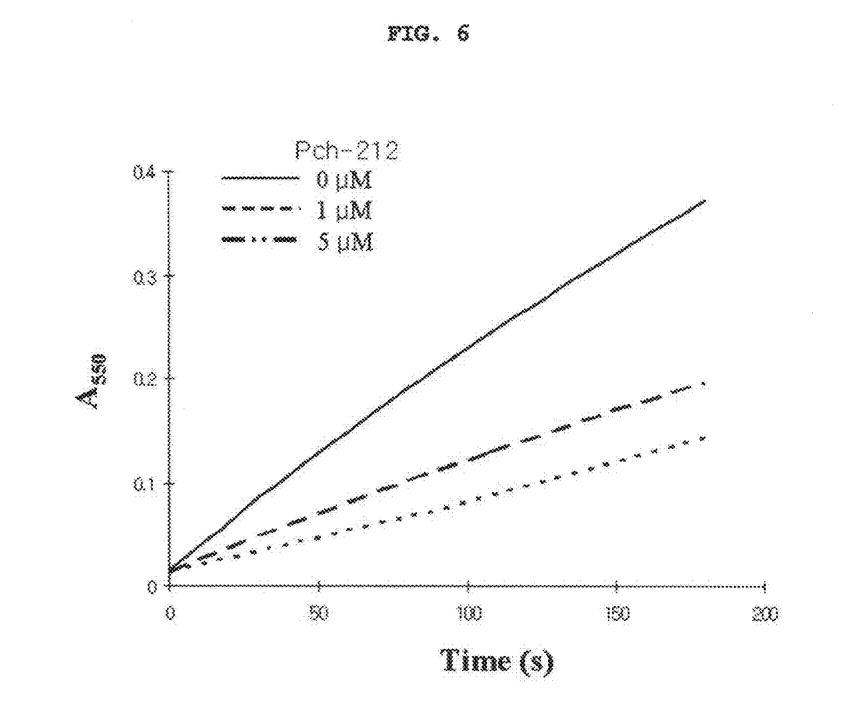
FIG. 6 is a graph showing the confirmation results for an antioxidant activity of an antioxidant Pch212 screened according to the present invention, by cytochrome reduction.

For analysis, a reaction buffer [50 mM potassium phosphate (pH 7.4)] was prepared. The buffer, 100 mM xanthine, 0.004 U of xanthine oxidase and an antioxidant Pch212 screened in Example 3 were introduced into a 5 mL glass bottle which was then sealed hermetically with a rubber stopper and purged with air. 20 μM cytochrome c was added thereto, and a degree of cytochrome c reduction was measured through an increased absorbance at 550 nm and transformed into a numerical value using an extinction coefficient of 21000 $M^{-1}$ $cm^{-1}$. Here, a superoxide anion-scavenging activity was confirmed by the difference of the degree of cytochrome c reduction (FIG. 6).

As apparent from the above description, the present invention is applicable to screen and commercialize low-toxic and effective antioxidants which will be used in various food and cosmetic additives as well as therapeutic medicines.

What is claimed is:

1. A method for screening an antioxidant with a mutant bacteria and chlorophyllide comprising:
   culturing, on an agar plate medium, a mutated bacteria, *Rhodobacter sphaeroides* 2.4.1 SodB 1, KCTC 11069BP, wherein said mutated bacteria has inhibited superoxide dismutase activity and wherein said mutated bacteria expresses chlorophyllide reductase;
   providing antioxidants to be screened on a plurality of filter discs;
   placing the plurality of filter discs on the agar plate medium; and
   selecting filter discs that have observed growth of the mutated bacteria; thereby screening for an antioxidant.

2. A method for screening an antioxidant with a mutant bacteria and chlorophyllide, comprising:
   culturing, on an agar plate medium, a mutated bacteria, *Rhodobacter sphaeroides* 2.4.1 SodB 1, KCTC 11069BP, wherein said mutated bacteria has inhibited superoxide dismutase activity and expresses chlorophyllide reductase;
   adding chlorophyllide to the agar plate medium;
   cutting the agar plate medium into blocks to form a plurality of chlorophyllide-added medium blocks;
   placing the plurality of chlorophyllide-added medium blocks on a Petri dish;
   providing an antioxidant to be screened and the mutated bacteria to the plurality of chlorophyllide-added medium blocks; and
   selecting the chlorophyllide-added medium blocks that have observed growth of the mutated bacteria.

3. The method of claim 1, wherein the mutated bacteria *Rhodobacter sphaeroides* 2.4.1 SodB 1, KCTC 11069BP is obtained by:
   disrupting a superoxide dismutase encoding gene sequence that is introduced into a first recombinant vector to inhibit superoxide dismutase activity;
   obtaining a second recombinant vector that over expresses a multimeric protein that induces production of superoxide anions in the presence of oxygen;
   transforming a first transformant *Escherichia coli* with the first recombinant vector and a second transformant *Escherichia coli* with the second recombinant vector; and
   conjugating the first transformant and the second transformant *Escherichia coli* with *Rhodobacter sphaeroides*.

4. The method of claim 1 or 2, wherein the mutated bacteria has an activity of producing superoxide anions while not producing hydrogen peroxide under an oxygen concentration of 1 to 3%.

5. The method of claim 1, wherein chlorophyllide added to the filter discs or the agar plate medium is in the range of 0.1 mM to 100 mM.

6. The method of claim 1, wherein the filter discs have a diameter of 5 to 20 mm and a thickness of 0.1 to 1 mm.

7. The method of claim 2, wherein chlorophyllide added to the agar plate medium is in the range of 0.1 mM to 100 mM.

8. The method of claim 2, wherein the medium blocks have a diameter of 10 to 30 mm and a thickness of 5 to 15 mm.

* * * * *